(12) United States Patent
Gay et al.

(10) Patent No.: US 9,242,753 B2
(45) Date of Patent: Jan. 26, 2016

(54) STERILIZABLE BIOPHARMACEUTICAL PACKAGING AND METHOD OF MAKING A STERILIZABLE BIOPHARMECEUTICAL PACKAGING

(75) Inventors: Isabelle Gay, Peypin (FR); Gaelle Nodin, Saint Maximin la Saint Baume (FR); Nicolas Mendyk, Peypin (FR); Stephanie Armau, Ossun (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 665 days.

(21) Appl. No.: 13/642,593

(22) PCT Filed: Feb. 11, 2011

(86) PCT No.: PCT/FR2011/050291
§ 371 (c)(1),
(2), (4) Date: Dec. 17, 2012

(87) PCT Pub. No.: WO2011/131870
PCT Pub. Date: Oct. 27, 2011

(65) Prior Publication Data
US 2013/0086871 A1 Apr. 11, 2013

(30) Foreign Application Priority Data
Apr. 20, 2010 (FR) ..................................... 10 52970

(51) Int. Cl.
*B65B 55/18* (2006.01)
*A61L 2/20* (2006.01)
(Continued)

(52) U.S. Cl.
CPC ............... *B65B 55/18* (2013.01); *A61L 2/0094* (2013.01); *A61L 2/20* (2013.01); *A61L 2/204* (2013.01);
(Continued)

(58) Field of Classification Search
CPC .... B65D 81/24; B65D 81/245; A23L 3/3445; A61L 2202/181; A61L 2/208; A61L 2/206; A61L 2/204; A61L 2/202; A61L 2/20; A61L 2/07; A61L 2/06; A61L 2/0094; B65B 55/18; B65B 55/12; B65B 55/02
USPC ......................................................... 206/439
See application file for complete search history.

(56) References Cited

U.S. PATENT DOCUMENTS 3,247,957 A * 4/1966 Kemble ........................ 206/440
4,296,862 A 10/1981 Armentrout et al.
(Continued)

FOREIGN PATENT DOCUMENTS

EP 1 520 795 4/2005
FR 2 820 118 8/2002
(Continued)

OTHER PUBLICATIONS

International Search Report dated Jun. 7, 2011, corresponding to PCT/FR2011/050291.

*Primary Examiner* — Stephen F Gerrity
(74) *Attorney, Agent, or Firm* — Young & Thompson (57) ABSTRACT

A sterilizable biopharmaceutical packaging includes an opening for inserting biopharmaceutical contents to be sterilized, the opening being separate from a sterilization gas conveyance channel so that the opening can be closed independently and before closing the sterilization gas conveyance channel. The opening is directly adjacent to an inner space for receiving the biopharmaceutical contents so that the contents to be sterilized are inserted directly into the inner space from outside the packaging. The elements for controlling the distribution of the sterilization gas open/close the sterilization gas conveyance channel independently of the opening or closing of the insertion opening. After sterilization, the outer wall, the sterilization gas conveyance channel, and the opening/closing element are capable of remaining rigidly connected therebetween so as to form a sterilized biopharmaceutical packaging that contains the sterilized biopharmaceutical contents and can be subjected to one or more integrity tests at any desired time after the sterilization.

22 Claims, 3 Drawing Sheets

(51) Int. Cl.
   *B65D 81/24*   (2006.01)
   *B65B 55/02*   (2006.01)
   *A61L 2/00*    (2006.01)
   *A61L 2/26*    (2006.01)

(52) U.S. Cl.
   CPC ................ *A61L 2/206* (2013.01); *A61L 2/208*
       (2013.01); *A61L 2/26* (2013.01); *B65B 55/02*
       (2013.01); *B65D 81/245* (2013.01); *A61L*
       *2202/181* (2013.01)

(56) References Cited

U.S. PATENT DOCUMENTS

| | | | |
|---|---|---|---|
| 4,583,643 A | 4/1986 | Sanderson | |
| 4,935,371 A * | 6/1990 | Rickloff | 435/304.3 |
| 4,936,456 A * | 6/1990 | Bell et al. | 206/439 |
| 5,230,430 A * | 7/1993 | Kidder | 206/484.1 |
| 5,524,755 A * | 6/1996 | Deeds | 206/370 |
| 7,040,485 B2 | 5/2006 | Gupta et al. | |
| 7,172,740 B2 * | 2/2007 | Gleichauf et al. | 422/300 |
| 7,387,205 B1 * | 6/2008 | Wilson | 206/524.4 |
| 2001/0033807 A1 | 10/2001 | Lin et al. | 422/33 |
| 2004/0081601 A1 * | 4/2004 | Morrissey et al. | 422/294 |
| 2005/0268573 A1 * | 12/2005 | Yan | 53/425 |
| 2007/0092398 A1 * | 4/2007 | McDonald | 422/28 |
| 2009/0217626 A1 * | 9/2009 | Kemp et al. | 53/407 |
| 2010/0303389 A1 * | 12/2010 | Armau et al. | 383/37 |
| 2011/0123396 A1 * | 5/2011 | Mermet et al. | 422/33 |
| 2011/0139650 A1 * | 6/2011 | Dworak | 206/363 |

FOREIGN PATENT DOCUMENTS

| | | |
|---|---|---|
| WO | 03/068274 | 8/2003 |
| WO | 2004/039419 | 5/2004 |
| WO | 2009/095572 | 8/2009 |

* cited by examiner

STERILIZABLE BIOPHARMACEUTICAL PACKAGING AND METHOD OF MAKING A STERILIZABLE BIOPHARMECEUTICAL PACKAGING

BACKGROUND OF THE INVENTION

1. Field of the Invention

The invention relates to sterilizable biopharmaceutical packages, and its object is more particularly a biopharmaceutical packaging that can be sterilized on the inside, a process for implementing such a packaging, and, finally, a unit that comprises a biopharmaceutical packaging and its sterilized biopharmaceutical contents.

2. Description of the Related Art

Here, biopharmaceutical is defined as that which relates to biotechnology or pharmacy.

It is known that, in the biopharmaceutical field, it is necessary to package biopharmaceutical contents that are brought in the sterile state in disposable, flexible packages for purposes of storage, shipping, handling, and transfer, for example into or from sterile chambers.

Biopharmaceutical contents such as those concerned here are in the solid state and capable of being handled and transferred. They may involve, for example, a sterile object such as a container, a container element such as a stopper, a syringe, but also elements for environmental control that are used within the framework of the biopharmaceutical process.

A first type of biopharmaceutical packaging that can be sterilized on the inside, capable of enclosing such biopharmaceutical contents to be sterilized comprising a flexible outer wall consisting of a part that is sealed against gases and pathogenic germs and a part that is permeable to a sterilization gas in the direction from the outside to the inside (namely, the direction extending from the outside to the inside of the packaging), is already known. Before sterilization, the sterilizable packaging comprises an opening for introduction of the biopharmaceutical contents to be sterilized from the outside to the inside of the packaging, with this introduction opening then being in the open state. This introduction opening is capable of being closed in an airtight manner once the biopharmaceutical contents are brought into the inside receiving space of the packaging. It is provided that after sterilization and at the time when this is desired, the sterilized packaging comprises an opening for extracting the sterilized biopharmaceutical contents, with this extraction opening then being in the open state, in such a way as to release the biopharmaceutical contents from the packaging for the purpose of the desired use. Previously, this extraction opening was closed in an airtight manner or was non-existent. It is also provided that the part of the outer wall that is permeable to sterilization gases is capable of being associated with, i.e., brought into communication with, a suitable source of sterilization gas, for example the sterilization gas of a sterilization chamber, in such a way that the sterilization gas that comes from the source in question is able to penetrate into the packaging by this permeable part. For implementing such a packaging, the biopharmaceutical contents that are to be sterilized are put into the inside receiving space of the packaging designed to enclose it, via the introduction opening previously opened and subsequently sealed in an airtight manner. Then, the sterilization gas is injected into the inside receiving space where the biopharmaceutical contents are located, via the part that is permeable to sterilization gas, which thus ensures the desired sterilization. At the time desired after sterilization, the opening for extracting the sterilized biophar-maceutical contents is opened in such a way as to extract said contents from the packaging so as to use them as desired.

In a nonlimiting manner, sterilization is defined here as the processes for sterilization by saturated water vapor, by dry heat, or else by toxic gases such as ethylene oxide (ETO), vapor-formaldehyde or else hydrogen peroxide ($H_2O_2$). During the sterilization of the biopharmaceutical contents, the environment surrounding the biopharmaceutical contents to be sterilized and the inside receiving space of the packaging that encloses the biopharmaceutical contents to be sterilized are filled with suitable sterilization gas, in such a way as to destroy, to a certain desired measure or in the required measurement, the pathogenic germs.

Sealed closing is defined as a closing sealed against gases, including water vapor, and pathogenic germs.

A part that is permeable to sterilization gas is defined as the capability of a separation element such as a wall, including a flexible wall such as a membrane, to allow the passage, at least in one direction, of a suitable sterilization gas, including in the form of vapor, such as water vapor.

In a first embodiment, the sterilization is carried out on the site of use of the biopharmaceutical contents, these thus packaged and sterilized contents then being ready for use and having to be used shortly after sterilization, in hopes that the integrity of the packaging has been preserved. Actually, with such an embodiment in which the permeable part remains permeable and in contact with the ambient atmosphere, even after sterilization, it is not possible to implement a process for monitoring the integrity of the packaging because of the presence of this permeable part. However, with such an embodiment, monitoring of integrity would be all the more necessary as the risk of deterioration of the permeable part after sterilization becomes high, in particular in the case of shipping or handling.

In a second embodiment, monitoring of integrity is done by placing the packaging that encloses the sterilized biopharmaceutical contents in an outer packaging pouch, with a differential pressure being created between the very interior of the packaging and the inside part of the outer packaging pouch that is outside of the packaging. This second embodiment has the drawback of requiring complicated handling and a significant amount of operating time to be able to detect a differential pressure change that signifies a loss of integrity.

It is known that in the biopharmaceutical field, it is essential to ensure that the flexible pouches are airtight, or at least have a degree of sealing that is deemed satisfactory. There are several integrity monitoring processes of such pouches.

The standard F 2095-01 of ASTM International whose title is "Standard Test Methods for Pressure Decay Leak Test for Nonporous Flexible Packages With and Without Restraining Plates" relates more specifically to the so-called pressure drop process. This process is envisaged according to two possible embodiments: with expansion limitation plates or without such plates. The document WO 2009/095572 relates to an integrity monitoring process in the case of a pouch with side gussets.

It is also known that in the biopharmaceutical field, it is common to use either pouches whose two large walls are directly joined to one another in such a way that once expanded, they have a limited volume and remain relatively thin, or pouches with gussets such that once expanded, they have a volume that can be much larger.

Consequently, with the first type of sterilizable biopharmaceutical packaging described above, the problem of the monitoring of integrity of the packaging is encountered, with the induced consequences: necessity of implementing sterilization on the site of use of the biopharmaceutical contents, necessity of quickly using the packaged and sterilized contents, or else implementation of a long and complex integrity monitoring.

A second type of packaging that corresponds to a closer state of the art is described in the document U.S. Pat. No. 7,040,485. Here, the packaging comprises a flexible outer wall, sealed against gases and pathogenic germs; an opening for introduction of the packaging of the biopharmaceutical contents to be sterilized from the outside to the inside, subsequently capable of being closed in an airtight manner; an inside space capable of receiving the biopharmaceutical contents; a sterilization gas conveyance channel from the outside of the packaging, comprising at least one upstream opening for intake of sterilization gas, toward the outside of the packaging, able to be associated in communication with a sterilization gas source, at least one downstream opening for distribution of sterilization gas that empties into the inside space, and a communication between the at least one upstream intake opening and the at least one downstream distribution opening; and, finally, means for control of the distribution of sterilization gas into the inside space.

In this second type of packaging, the outer wall is a sheath that comprises a first segment and a second segment that are adjacent to the location of a side that is open before sterilization and closed during sterilization. On one of its two surfaces, the first sheath segment comprises a part that is permeable to sterilization gas belonging to a sterilization gas conveyance channel from the outside of the packaging. The first sheath segment also comprises an end opening for introduction into the packaging of the biopharmaceutical contents to be sterilized, then in the open state. This introduction opening is located opposite the open side. The second sheath segment is closed on its periphery, except for the open side before sterilization, and closed during sterilization. The second sheath segment forms an inside space for receiving biopharmaceutical contents to be sterilized. The packaging also comprises means for control of the distribution of sterilization gas in the inside space so that it accesses or it can access the environment enveloping the contents to be sterilized and the inside space of the packaging that encloses it. For the implementation of such a packaging, the biopharmaceutical contents to be sterilized are introduced into the packaging by passage through the end introduction opening, and then by crossing the first segment, namely passage in front of the segment that is permeable to sterilization gas and passage through the open side. Thus, the biopharmaceutical contents access the inside receiving space in which it is placed for sterilization. The end introduction opening is then sealed on itself and thus closed, while the side is kept open. The sterilization gas is then introduced into the packaging, from the outside of the packaging, through the permeable part. Thus, the sterilization gas penetrates into the first sheath segment and then, passing through the open side, penetrates into the second sheath segment. The sterilization of the biopharmaceutical contents is thus ensured. The open side is then sealed on itself and thus closed. The packaging is then split into two, with the two sheath segments being separated, the sheath being cut crosswise toward the open side that was previously sealed.

Thus, with this second type of packaging, the open side serves both in the introduction of the biopharmaceutical contents to be sterilized and in the sterilization gas conveyance channel. Consequently, the open side that is adjacent to the inside space cannot be closed independently and before the closing of the sterilization gas conveyance channel.

In contrast, the opening for introduction of the biopharmaceutical contents to be sterilized is separated from the inside space for receiving the biopharmaceutical contents to be sterilized and the sterilized biopharmaceutical contents, in such a way that the biopharmaceutical contents to be sterilized are introduced into the inside space from the outside of the packaging only in an indirect manner. Such an embodiment is therefore problematic to implement in some cases, taking into account the shape or the size of the packaging or the nature, the shape and the size of the biopharmaceutical contents.

The same drawback is encountered with the packages described in the documents WO 2004/039419 and FR-A-2820118.

Also, the control means for the distribution of sterilization gas are opening/closing means of the side that participates in the introduction of contents to be sterilized in the packaging, in such a way that the sterilization gas conveyance channel cannot be opened or closed independently of the opening or closing of the introduction of the contents to be sterilized.

Finally, once the sterilization is done, the outer wall, the sterilization gas conveyance channel and the opening/closing means are necessarily separated into two. Taking into account that in the sterilized packaging, there is no longer a permeable part, the latter having been removed, it is possible to implement a process for monitoring the integrity of the packaging whose wall is made airtight in manufacturing and which is expected to remain airtight. However, this possibility of implementing an integrity monitoring process is achieved only at the expense of cutting the packaging for separating the two sheath segments. However, such an operation for cutting the sheath is always difficult because, specifically, it may compromise the integrity of the packaging.

Consequently, with the second type of sterilizable biopharmaceutical packaging described above, the problem of the difficulty of passing the biopharmaceutical contents into the inside space and the problem of the risk of deterioration of the integrity of the packaging as a result of its being cut are encountered.

The document U.S. Pat. No. 4,583,643 that describes a flexible packaging designed to receive items that can be automatically sterilized in such a way as to ensure their integrity is also known from the state of the art. The flexible packaging has a first module that forms a valve and an actuator positioned on the upper wall and a second module that forms a valve and an actuator positioned on the lower wall. Each of these modules that forms a valve and an actuator is equipped with a support part that comprises a large number of holes acting as openings so as to allow the passage of a fluid flow inside and outside of the flexible packaging and a valve that is used to reclose the holes.

The document U.S. Pat. No. 4,296,862 that describes a part that is designed to constitute a sterile barrier so as to keep the interior of a packaging device under sterile conditions is known.

The document WO 03/068274 that relates to a system that makes it possible to inject ozonized gas inside a packaging that contains an object to be disinfected or sterilized is also known. The packaging comprises coupling means that make it possible for it to be combined with said injection system to ensure the introduction of ozonized gas into the chamber that receives the object to be sterilized, as well as closing means that make it possible to ensure the sealing of the chamber when the packaging is no longer associated with the system.

Furthermore, the document EP 1 520 795 that describes a packaging for pharmaceutical products that is formed from a first impermeable foil, a second impermeable foil welded to the first, and a permeable clasp welded to the second foil and able to be welded to the first foil is known. These three foils form an inside space into which an object can be introduced for the purpose of its sterilization. When said sterilization operation is terminated, the portion of the packaging containing the permeable clasp is cut into sections, and the first and second impermeable foils are welded to one another in such a way as to constitute an inside space delimited only by these first and second impermeable foils. As above, such a cutting operation is dangerous because it can compromise the integrity of the packaging.

SUMMARY OF THE INVENTION

The invention therefore has as its object, in the case of a sterilizable biopharmaceutical packaging that is capable of enclosing biopharmaceutical contents to be sterilized, to remedy the known drawbacks and limits of the packages and to provide a solution, in combination, to the following three problems:

- Possibility of introducing, in a simple way, the biopharmaceutical contents directly into the inside space of the packaging with the necessity of passing through another compartment,
- Possibility of not having to cut the packaging into sections once the sterilization is done,
- Possibility of implementing integrity monitoring of the packaging with differential pressure that is fast and can take place at any time from the sterilization, in any case does not necessarily have to take place on the site of use of the biopharmaceutical contents and just before use.

The invention also has as its object to attain these objectives with means that are simple, inexpensive, and easy to use.

For this purpose, and according to a first aspect, the invention has as its object a sterilizable biopharmaceutical packaging, capable of enclosing biopharmaceutical contents to be sterilized, comprising:

- An outer wall that is flexible and sealed against gases and pathogenic germs,
- An opening for introduction of the biopharmaceutical contents to be sterilized from the outside to the inside of the packaging, as a result capable of being closed in an airtight manner,
- An inside space that is capable of receiving the biopharmaceutical contents,
- A sterilization gas conveyance channel from the outside of the packaging, comprising at least one upstream opening for intake of sterilization gas toward the outside of the packaging, capable of being associated in communication with a sterilization gas source, at least one downstream opening for distribution of sterilization gas emptying into the inside space, and a communication between the at least one upstream intake opening and the at least one downstream distribution opening,
- And means for control of the distribution of sterilization gas in the inside space.

Such a packaging is such that:

- The opening for introduction of the biopharmaceutical contents to be sterilized is separate from the sterilization gas conveyance channel, in such a way that the opening for introduction of the biopharmaceutical contents to be sterilized can be closed independently and before the closing of the sterilization gas conveyance channel,
- The opening for introduction of the biopharmaceutical contents to be sterilized is directly adjacent to the inside space for receiving the biopharmaceutical contents to be sterilized and the sterilized biopharmaceutical contents, in such a way that the biopharmaceutical contents to be sterilized are introduced directly into the inside space from the outside of the packaging,
- The means for control of the sterilization gas distribution are opening/closing means of the sterilization gas conveyance channel, in such a way that the sterilization gas conveyance channel can be opened or closed independently of the opening or closing of the introduction opening,
- Once the sterilization is done, the outer wall, the sterilization gas conveyance channel, and the opening/closing means are capable of remaining integral with one another in such a way as to form a sterilized biopharmaceutical packaging that encloses the sterilized biopharmaceutical contents that can undergo one or more integrity tests at any time desired after sterilization.

With such a packaging, it is possible to introduce, in a simple manner, the biopharmaceutical contents directly into the inside space of the packaging without the necessity of passing through another compartment, it is possible to not have to cut the packaging into sections once the sterilization is done, and, finally, it is also possible to implement monitoring of integrity of the packaging with differential pressure that is fast and can take place at any time from the sterilization; in any case, it does not necessarily have to take place on the site of use of the biopharmaceutical contents and just before use.

According to a first embodiment, the sterilization gas conveyance channel includes at least one large-surface membrane that is permeable to the sterilization gas and that forms a downstream opening for distribution of sterilization gas distributed over the surface of the membrane, with the membrane that is permeable to sterilization gas forming a portion of the envelope of the inside space also constituting a means capable of stopping any pathogenic germs.

According to a first embodiment, a membrane that is permeable to sterilization gas is separate from the outer wall of the packaging and connected to it, in it, and made integral with it in an airtight manner, with the outer wall comprising a ring-bounded upstream opening for intake of sterilization gas, with communication existing between the upstream intake opening and the membrane.

As appropriate, the membrane that is permeable to the sterilization gas extends substantially opposite the upstream intake opening or else it extends over at least substantially the entire length of the outer wall of the packaging.

According to this first embodiment, the opening/closing means are a stoppering element mounted to move on or to be detached from the ring of the upstream opening for intake of sterilization gas.

According to a second embodiment, a membrane that is permeable to sterilization gas consists of a permeable zone of the outer wall of the packaging that belongs to a deployable/foldable part of the outer wall of the packaging and that forms the sterilization gas conveyance channel, with this deployable/foldable part being capable of being either deployed in such a way that the sterilization gas conveyance channel is open, or folded on itself toward the inside of the packaging in such a way that the sterilization gas conveyance channel is closed.

As appropriate, the part of the outer wall of the packaging that is capable of being either in the deployed state or in the state folded on itself toward the inside is a longitudinal gusset of the outer wall or a transverse end part of the outer wall.

According to one embodiment, the opening/closing means consist of the outer wall itself, of which the deployable/foldable part, where the zone that is permeable to the sterilization gas is found, is inserted between two airtight facing side parts located on both sides of the deployable/foldable part, in such a way that when the deployable/foldable part is folded on itself toward the inside of the packaging, the two facing side parts, then located opposite and close together, are capable of being sealed to one another on their outer periphery in an airtight manner, around the zone that is permeable to the sterilization gas, in such a way as to prevent the sterilization gas from accessing the permeable zone.

According to a second embodiment, the sterilization gas conveyance channel includes at least one segment of a sterilization gas intake tube, located on the outside of the packaging, forming upstream an upstream opening for intake of sterilization gas and downstream a downstream opening for distribution of sterilization gas provided in the outer wall, the segment of the sterilization gas intake tube being integral with the outer wall in an airtight manner, at least one means that can stop any pathogenic germs, such as a filtering cartridge, being inserted in the segment of a sterilization gas intake tube between the upstream intake opening and the downstream distribution opening.

In this case, according to one embodiment, the opening/closing means of the sterilization gas conveyance channel are a means for stopping the stream that is mounted to move on or be detached from the segment of the sterilization gas intake tube, in particular a closing clamp or a transverse weld.

According to one embodiment, the inside space extends over substantially the entire length of the outer wall in the form of a sheath, and the opening for introduction of the biopharmaceutical contents to be sterilized is located at one end of the outer wall in the form of a sheath.

According to one embodiment, the at least one upstream opening for intake of gas and the opening for introduction of the biopharmaceutical contents to be sterilized are separated from one another.

According to one development, the packaging also comprises at least one gas inlet/outlet end fitting, mounted on the outer wall, in communication with the inside space, capable of being brought into the open state or into the closed state by actuating closing means, in such a way as to make it possible to enable a functional gas to enter into or exit from the inside space.

According to one embodiment, the biopharmaceutical packaging also comprises an opening that is delimited by an annular flange on which is mounted a movable or detachable means of aseptic transfer, such as a movable or detachable door for aseptic transfer of the double-door type.

In this case, according to a first variant embodiment, the movable or detachable means for aseptic transfer works with the introduction opening and is capable of ensuring the closing of this introduction opening in an airtight manner.

In this case, according to a second variant embodiment, the movable or detachable means for aseptic transfer works with a portion of the outer wall that is separate from the membrane that is permeable to sterilization gas in such a way as to form a secondary opening that can be opened and then closed in an airtight manner.

According to a second aspect, the invention has as its object a process for implementing a sterilizable biopharmaceutical packaging as has been described above for the purpose of containing and sterilizing biopharmaceutical contents therein, in which:

Such a packaging, empty of biopharmaceutical contents, and whose introduction opening is open, is used,
The biopharmaceutical contents to be sterilized are used,
A sterilization gas source is used,
Via the introduction opening, the biopharmaceutical contents to be sterilized are introduced directly into the inside receiving space,
Then, the introduction opening is closed in an airtight manner,
Then, whereas the sterilization gas conveyance channel is open, the sterilization gas is brought in from the sterilization gas source to the inside receiving space where the biopharmaceutical contents to be sterilized are located in such a way as to sterilize the biopharmaceutical contents,
Then, the opening/closing means are implemented in such a way as to close the sterilization gas conveyance channel,
and thus a sterilized biopharmaceutical packaging that encloses the sterilized biopharmaceutical contents that can undergo one or more integrity tests at any time desired after sterilization is formed.

According to one embodiment, a biopharmaceutical packaging as described is used, with a membrane that is permeable to sterilization gas that is separate from the outer wall, and opening/closing means that are a stoppering element are used. In this case, after the biopharmaceutical contents have been sterilized, the stoppering element is implemented on a ring of the upstream opening for intake of sterilization gas in such a way as to close the sterilization gas conveyance channel.

According to one embodiment, a biopharmaceutical packaging is used as described, with a membrane that is permeable to sterilization gas constituted by a permeable zone of the outer wall of the packaging belonging to a deployable/foldable part, and opening/closing means that consist of the outer wall whose deployable/foldable part is inserted between two airtight facing side parts are used. In this case, after the biopharmaceutical contents have been sterilized, the deployable/foldable part is folded on itself toward the inside of the packaging, in such a way that the two facing side parts are located opposite and close together, and they are sealed to one another on their outer periphery in an airtight manner, around the zone that is permeable to the sterilization gas, in such a way as to close the sterilization gas conveyance channel.

According to one embodiment, a biopharmaceutical packaging is used as described, with a segment of a sterilization gas intake tube, and opening/closing means of the sterilization gas conveyance channel, being a means for stopping the flow, are used. In this case, after the biopharmaceutical contents have been sterilized, the means for stopping the flow is inserted on the segment of the sterilization gas intake tube in such a way as to close the sterilization gas conveyance channel.

According to one embodiment, once the sterilization is done, the outer wall, the sterilization gas conveyance channel and the opening/closing means are kept integral in such a way as to form the sterilized biopharmaceutical packaging that encloses the sterilized biopharmaceutical contents.

According to one characteristic, once the sterilization is done, the biopharmaceutical packaging is not cut into multiple segments.

According to one development, at any time desired after sterilization, the sterilized biopharmaceutical packaging that encloses the sterilized biopharmaceutical contents is subjected to one or more integrity tests of the type requiring sealing of the packaging against gas.

According to a third aspect, the invention has as its object a sterilized biopharmaceutical packaging that encloses sterilized biopharmaceutical contents, obtained by the implementation of the process as described, with the packaging also comprising an opening for extracting the sterilized biopharmaceutical contents from the inside to the outside of the packaging, closed in an airtight manner and as a result capable of being opened so as to extract the biopharmaceutical contents from the inside space.

BRIEF DESCRIPTION OF THE DRAWING FIGURES

Now, several embodiments of the invention will be described using drawings, in which:

FIGS. 5A and 5B are two views, respectively front and perspective, and a profile elevation of a second example of the same second embodiment of a sterilizable biopharmaceutical packaging, in which the part of the outer wall of the packaging that is capable of being either in the deployed state or in the state folded on itself toward the inside is formed by two transverse end parts of the outer wall, with the means for control of the distribution of sterilization gas in the inside space opening the sterilization gas conveyance channel in the case of FIG. 5a, with the deployable/foldable part of the outer wall of the packaging being deployed here, whereas the means for control of the distribution of sterilization gas in the inside space close the sterilization gas conveyance channel in the case of FIG. 5B, with the deployable/foldable part of the outer wall of the packaging being folded on itself here toward the inside of the packaging.

FIGS. 8A, 8B, and 8C are three respective front views that illustrate successive stages of the implementation of a packaging according to the second example of the second embodiment of FIGS. 3 and 4, namely—before sterilization—the introduction of the contents to be sterilized in the inside space of the packaging by the open introduction opening (FIG. 8A), for and during sterilization, with the sterilization gas intake in the inside space, the conveyance channel being open, the means for control of the distribution of sterilization gas in the inside space opening of this channel (FIG. 8B), after sterilization, the closing of the sterilization gas conveyance channel, the two longitudinal gussets of the sterilized packaging forming the deployable/foldable part being folded on themselves toward the inside of the packaging and sealed on their periphery.

DETAILED DESCRIPTION OF THE INVENTION

Figure 1:
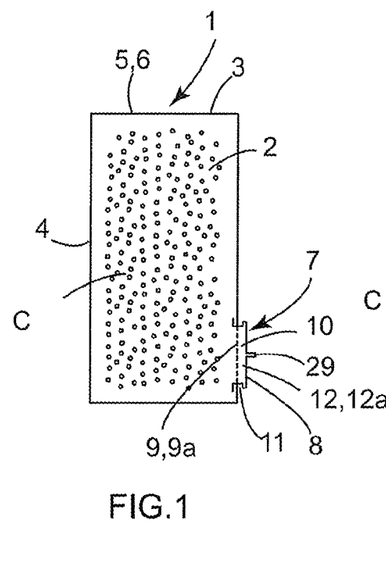
FIG. 1 is a front view of a first example of a first embodiment of a sterilizable biopharmaceutical packaging whose inside space is filled with biopharmaceutical contents to be sterilized, having a sterilization gas conveyance channel from the outside of the packaging including a membrane that is permeable to the sterilization gas separate from the outer wall of the packaging and connected to it and made integral with it in an airtight manner, and means for control of the distribution of sterilization gas in the inside space here closing the sterilization gas conveyance channel, with the introduction opening from the outside to the inside of the packaging of the biopharmaceutical contents to be sterilized being closed here.

Reference is made to FIG. 1 that illustrates a sterilizable biopharmaceutical packaging 1 according to a first implementation, a first embodiment, and a first variant, whose inside space 2 is filled with biopharmaceutical contents to be sterilized C.

Of course, the inside space 2 is adapted, in particular in size, to the biopharmaceutical contents to be sterilized C that it is to receive and enclose.

The packaging 1 comprises a flexible outer wall 3, sealed against gases and pathogenic germs, for example, made of plastic such as polyethylene or polypropylene.

Such an outer wall 3 is, for example, of the type formed by two large surfaces of a general rectangular shape, joined to one another on their periphery 4, except for a transverse end edge 5, in such a way as to constitute a so-called "2D" pouch (D meaning dimensions), well known in the biopharmaceutical field. Such a packaging 1 is well suited to biopharmaceutical contents to be sterilized C of relatively limited size.

The transverse end edge 5 is originally in the open state. It thus constitutes an introduction opening 6 from the outside to the inside of the packaging 1 of the biopharmaceutical contents to be sterilized C. Below, i.e., once the biopharmaceutical contents to be sterilized C are placed in the inside space 2, the introduction opening 6 is closed in an airtight manner, for example by sealing, with the constituent material of the outer wall 3 being thermosealable on itself.

Because of the structure that was just described, the introduction opening 6 is directly adjacent to the inside space 2. Consequently, the biopharmaceutical contents to be sterilized C can be introduced directly into the inside space 2 from the outside of the packaging 1.

The packaging 1 also comprises a sterilization gas conveyance channel 7 from the outside of the packaging 1.

The sterilization gas conveyance channel 7 comprises here an upstream opening 8 for intake of sterilization gas, located toward the outside of the packaging 1. This intake opening 8 is capable of being associated in communication with a sterilization gas source, such as, for example, the environment prevailing in a sterilization chamber.

The sterilization gas conveyance channel 7 also comprises a large number of downstream openings 9 for distribution of sterilization gas emptying into the inside space 2.

Finally, the sterilization gas conveyance channel 7 comprises a communication 10 between the upstream intake opening 8 and the distribution openings 9.

The conveyance channel 7 is separate from the introduction opening 6, and, conversely, the introduction opening 6 is separate from the conveyance channel 7. In so doing, the introduction opening 6 can be closed independently and before the closing of the conveyance channel 7.

In the embodiment of FIG. 1, the upstream intake opening 8 is formed by an opening that is provided in the outer wall 3. This opening 8 is bounded by a ring 11.

In contrast, in this embodiment, the conveyance channel 7 includes a membrane 9a that is permeable to sterilization gas, which membrane 9a forms the large number of downstream distribution openings 9.

The membrane 9a is separate from the outer wall 3. It is placed in the packaging 1 itself. It is connected to the outer wall 3 and made integral with it in an airtight manner, for example by sealing.

Such a membrane 9a is made of, for example, a material such as the one that is known under the trademark TYVEK®. It is a non-woven textile of high-density polyethylene fibers, which, after extrusion, are organized in a random and consolidated manner, with the resulting sheet being porous in a selective manner, here with the sterilization gas that it is to allow to pass in the direction extending from the outside to the inside. The material that is known under the trademark TYVEK® does not exclude others also having a permeability that is selective to the sterilization gas.

The porosity and the selective permeability of the membrane 9a constitute the distribution openings 9 or all of the distribution openings 9.

It should be pointed out here that to the extent that the membrane 9a has a porosity and a selective permeability relative to the sterilization gas, the latter can be capable of allowing this sterilization gas to pass not only in the direction extending from the outside to the inside but also in the direction extending from the inside to the outside. Thus, the membrane 9a can form a large number of downstream distribution openings 9 that make possible, on the one hand, the introduction of the sterilization gas into the inside space 2 of the biopharmaceutical packaging 1, and, on the other hand, the output of this same distribution gas toward the communication 10 and the upstream intake opening 8.

The advantage of using a membrane 9a therefore also resides in the fact that it is not necessary to use means for evacuating sterilization gas that are separate and independent of the sterilization gas intake means at the end of the sterilization operation for extracting the sterilization gas from the inside space of the chamber.

The membrane 9a extends substantially opposite the upstream intake opening 8. The large-surface membrane 9a thus forms, opposite the upstream intake opening 8, a portion of the envelope 2a of the inside space 2. With this structure, the communication 10 forms a type of limited cylinder bound at the ends by the membrane 9a and by the upstream intake opening 8 and whose diameter is that of the membrane 9a and the opening 8.

Such a membrane 9a makes it possible not only to distribute the sterilization gas from the entire surface of the membrane, but it also constitutes a means that is capable of stopping any pathogenic germs.

The packaging 1 also comprises means 12 for control of the distribution of sterilization gas in the inside space 3.

The means 12 for control of the distribution of sterilization gas are opening/closing means 12 of the intake channel 7, in such a way that the conveyance channel 7 can be opened or closed independently of the opening or closing of the introduction opening 6.

In this case, the opening/closing means 12 come in the form of a stoppering element 12a that is mounted to move on or to be detached from the ring 11. Such a stoppering element 12a can consist of a part in the form of an airtight wall fixed on the ring by means of a closing system such as the one that is known under the name and the trademark TRI-CLAMP® or any other attachment system.

The process for implementing the packaging 1 that was just described is designed to enclose therein biopharmaceutical contents to be sterilized C and to sterilize them.

In this process, such a packaging 1 is used with a membrane 9a that is permeable to sterilization gas, separate from the outer wall 3, empty of the biopharmaceutical contents to be sterilized C, and whose introduction opening 6 is open. Opening/closing means 12, here the stoppering element 12a, are used. Also, a sterilization gas source is used. Finally, the biopharmaceutical contents to be sterilized C that are to be sterilized are used.

Via the introduction opening 6, the biopharmaceutical contents to be sterilized C are introduced directly into the inside receiving space 2.

Then, the introduction opening 6 is closed in an airtight manner by sealing the heretofore open transverse edge 5.

Then, whereas the conveyance channel 7 is open, because the stoppering element 12a that constitutes the opening/closing means 12 is removed, which in any case is inactive relative to the stoppering function, the sterilization gas is brought from the sterilization gas source into the inside space 2 where the biopharmaceutical contents to be sterilized C are located. It is thus that the biopharmaceutical contents are sterilized.

The sterilization gas can then be withdrawn from the inside space 2 by passing through the sterilization gas conveyance channel 7 that then constitutes a sterilization gas evacuation channel toward the communication 10, the upstream intake opening 8, and the outside.

From biopharmaceutical contents to be sterilized C, it becomes sterilized biopharmaceutical contents C.

Once the sterilization is done, the stoppering element 12a is used in such a way as to close the intake channel 7, and, for this purpose, it is placed on the ring 11 of the upstream opening 8 for intake of sterilization gas.

A sterilized biopharmaceutical packaging 1 that encloses the sterilized biopharmaceutical contents C is then formed.

The sterilized biopharmaceutical packaging 1 consists of the outer wall 3, the sterilization gas conveyance channel 7, and the opening/closing means 12, in this case the stoppering element 12a, which remain integral with one another and enclose the sterilized biopharmaceutical contents C.

With this arrangement, this sterilized biopharmaceutical packaging 1 and the sterilized biopharmaceutical contents C can undergo one or more integrity tests at any time desired after sterilization, either immediately or shortly after manufacture, or immediately or shortly before use, or else at several times.

Figure 2:
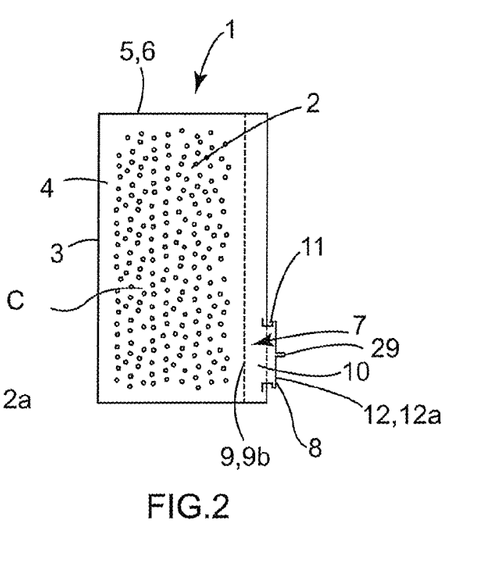
FIG. 2 is a view that is analogous to FIG. 1 of a second example of the same first embodiment of sterilizable biopharmaceutical packaging.

Reference is made to FIG. 2, which illustrates a sterilizable biopharmaceutical packaging 1 according to the same first implementation, the same first embodiment, but a second variant.

In this second variant, contrary to the first variant of FIG. 1, the membrane 9b that is permeable to sterilization gas extends over substantially the entire length of the outer wall 3 of the packaging 1, and not only opposite the upstream intake opening 8. With this structure, the communication 10 extends over substantially the entire length of the outer wall 3 toward the membrane 9a and over the diameter of the upstream intake opening 8, toward the latter. In addition, the membrane 9b is separated relative to a corresponding part of the outer wall 3 in such a way as to form a sort of corridor that makes it possible for the sterilization gas to supply the entire surface of the permeable membrane 9a.

This structural arrangement makes it possible to distribute the sterilization gas that directly penetrates into the inside space 2 properly over a large surface of its envelope.

The implementation of such a packaging 1 with a membrane 9b that is permeable to the sterilization gas is analogous to the one described above for the packaging 1 with a membrane 9a that is permeable to sterilization gas.

Reference is made to FIGS. 3, 4, 5A, 5B, 6, 8A, 8B and 8C that illustrate, still within the framework of the first embodiment that provides a membrane 9 that is permeable to sterilization gas, a second embodiment in which the membrane consists of a permeable zone of the outer wall 3 of the packaging 1.

Reference is made more especially to FIGS. 3, 4, 8A, 8B and 8C, which illustrate a first variant of this second embodiment.

Figure 3:
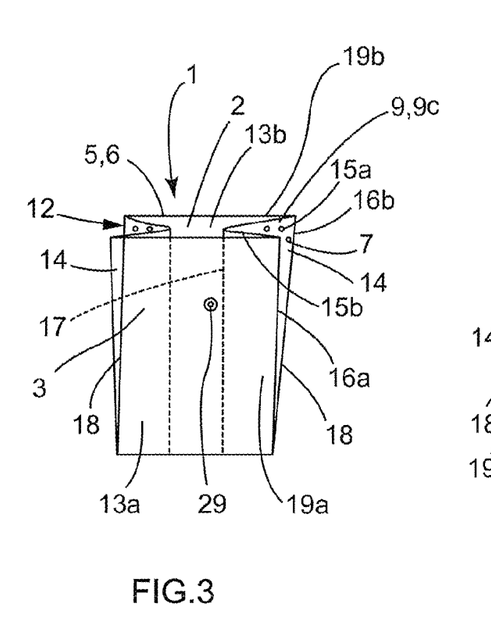
FIG. 3 is a front, perspective view of a first example of a second embodiment of a sterilizable biopharmaceutical packaging that has a sterilization gas conveyance channel from the outside of the packaging including a membrane that is permeable to the sterilization gas consisting of a permeable zone of the outer wall of the packaging belonging to a deployable/foldable part of the outer wall of the packaging that is a longitudinal gusset of the outer wall, and means for control of the distribution of sterilization gas in the inside space here opening the sterilization gas conveyance channel, with the opening for introducing the biopharmaceutical contents to be sterilized from the outside to the inside of the packaging being open here.

In this first variant, the outer wall 3 comprises two large surfaces 13a and 13b, here in a general rectangular shape, joined to one another by two longitudinal gussets 14, each comprising two flaps 15a and 15b, adjacent to the two large surfaces 13a and 13b by two lateral folding lines 16a and 16b, while the two flaps 15a and 15b are adjacent to one another by a median folding line 17.

The two flaps 15a and 15b of the same longitudinal gusset 14 have the same transverse width that is less than the transverse width of the large surfaces 13a and 13b. In contrast, the two flaps 14 are located toward the inside of the packaging, i.e., the two flaps 15a and 15b and the median folding line 17 are located opposite the two large surfaces 13a and 13b, when the packaging 1 is folded flat.

Such a structure or different but analogous structures make it possible to constitute pouches with gussets that can be folded flat or deployed unfolded.

In the first variant embodiment considered, a membrane 9c is provided that is permeable to sterilization gas that belongs to a deployable/foldable part 18 of the outer wall 3 of the packaging 1, namely more specifically the longitudinal gussets 14, the deployable/foldable part 18 being double here. Of course, a single deployable/foldable part 18 can be provided.

The membrane 9c forms the sterilization gas conveyance channel 7.

Figure 4:
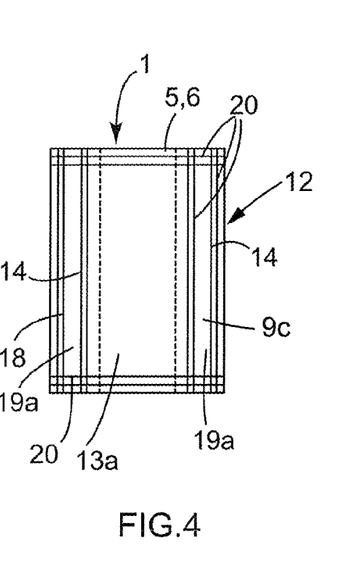
FIG. 4 is a front view of the biopharmaceutical packaging of FIG. 3, once sterilized, the means for control of the distribution of sterilization gas in the inside space here closing the sterilization gas conveyance channel, with the opening for introducing the biopharmaceutical contents to be sterilized from the outside to the inside of the packaging also being closed here.

As indicated, the deployable/foldable part 18, i.e., the longitudinal gussets 14, forming the membrane 9c, is capable of being either deployed in such a way that the sterilization gas conveyance channel 7 is open or folded on itself toward the inside of the packaging 1 in such a way that the sterilization gas conveyance channel 7 is then closed.

With this packaging variant 1, the means 12 for control of the distribution of sterilization gas are, here also, opening/closing means 12 of the conveyance channel 7, but the latter consist of the outer wall 3 itself, including the deployable/foldable part 18, double, i.e., each longitudinal gusset 14, where the membranes 9c that are permeable to the sterilization gas are located, is inserted between two facing side parts 19a and 19b, airtight, formed by the parts of the large surfaces 13a and 13b that are adjacent to each flap 15a and 15b, where the lateral folding lines 16a and 16b are located.

With this structure, when the deployable/foldable part 18, double, is folded on itself toward the inside of the packaging 1, the two facing side parts 19a and 19b are located opposite and close together.

They are then capable of being sealed on one another at their outer periphery 20, in an airtight manner, around the zone 9c that is permeable to the sterilization gas in the form of membrane 9c. With such a structure, in this case, the two facing side parts 19a and 19b prevent the sterilization gas from accessing the zone 9c that is permeable to the sterilization gas in the form of membrane 9c.

Figures 7, 8A, 8B, 8C:
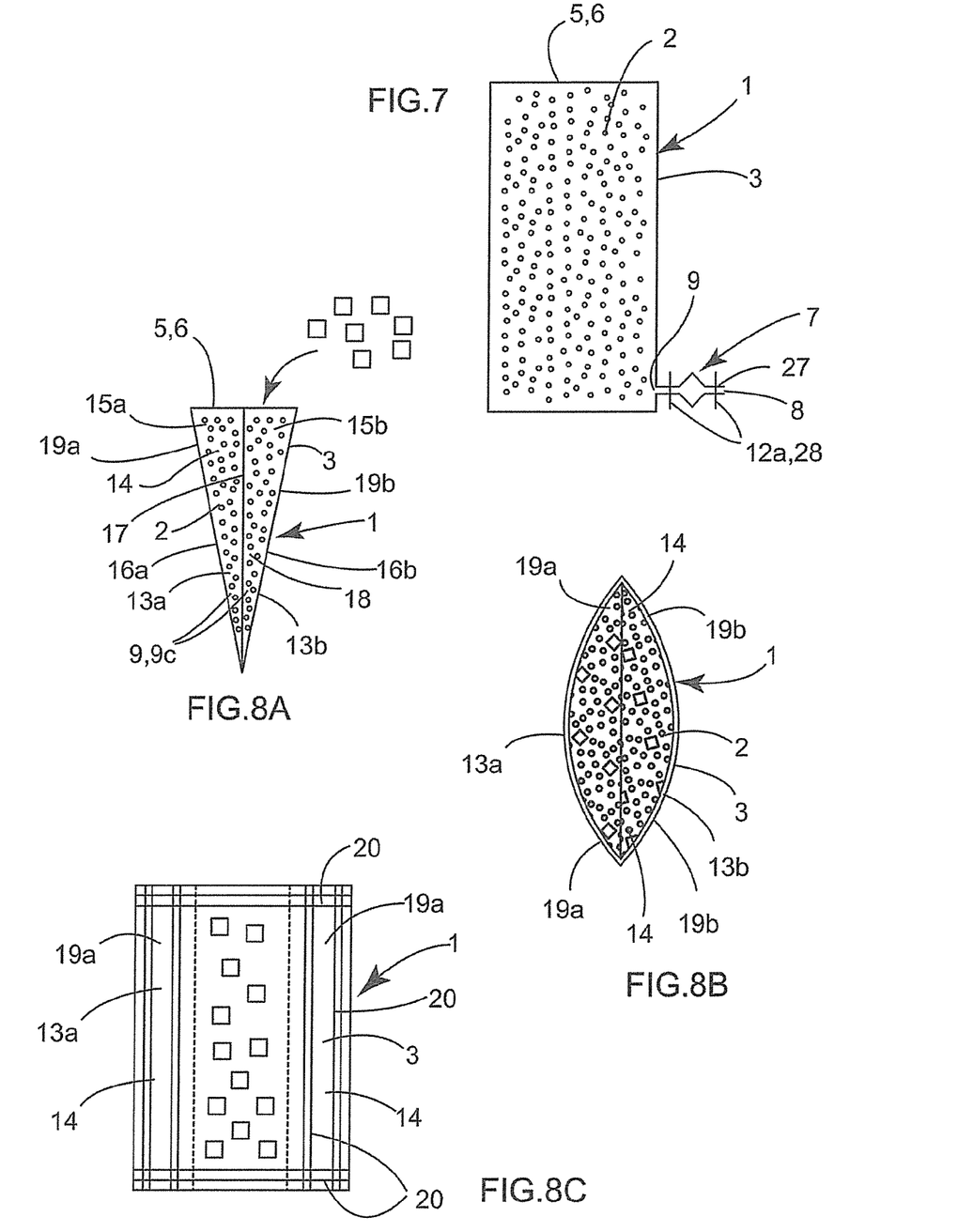
FIG. 7 is a front view of an example of a second embodiment of a sterilizable biopharmaceutical packaging, having a sterilization gas conveyance channel from the outside of the packaging including a segment of a sterilization gas intake tube, located on the outside of the packaging, forming upstream an upstream opening for intake of sterilization gas and downstream a downstream opening for distribution of sterilization gas provided in the outer wall, the segment of a sterilization gas intake tube being made integral with the outer wall in an airtight manner, a means that is capable of stopping any pathogenic germs from being inserted into the segment of the sterilization gas intake tube between the upstream intake opening and the downstream distribution opening.

The process for implementing such a packaging 1 is such that such a packaging 1, with a membrane 9c that is permeable to the sterilization gas that is formed by a portion of the outer wall 3, empty of the biopharmaceutical contents to be sterilized C, and whose introduction opening 6, located at one end, is open, is used. Opening/closing means 12, here the outer wall 3 itself and more specifically still the two facing side parts 19a and 19b, are used. Also, a source of sterilization gas is used. Finally, the biopharmaceutical contents to be sterilized C are used.

Via the introduction opening 6, the biopharmaceutical contents to be sterilized C are introduced directly into the inside receiving space 2.

Then, the introduction opening 6 is closed in an airtight manner, by sealing the transverse edge 5 until open here.

Then, whereas the conveyance channel 7 is open, because the outer wall 3 is deployed, in such a way that the opening/closing means 12, here the two facing side parts 19a and 19b, are inactive relative to the stoppering function, the sterilization gas is brought from the sterilization gas source into the inside space 2, where the biopharmaceutical contents to be sterilized C are located. It is thus that the biopharmaceutical contents are sterilized.

In the same way as above, the sterilization gas can then be withdrawn from the inside space 2 by passing through the sterilization gas conveyance channel 7 that then constitutes a sterilization gas evacuation channel toward the outside.

From biopharmaceutical contents to be sterilized C, they become sterilized biopharmaceutical contents C.

Once the sterilization is done, the deployable/foldable part 18, i.e., the gussets 14, is folded on itself toward the inside of the packaging 1.

As a result, the two facing side parts 19a and 19b of each gusset 14 are located opposite and close together. It is then possible to seal them to one another on their outer periphery 20, in an airtight manner, in such a way as to close the sterilization gas conveyance channel 7.

A sterilized biopharmaceutical packaging 1 that contains the sterilized biopharmaceutical contents C is then formed.

As for the first embodiment of the first implementation, the sterilized biopharmaceutical packaging 1 consists of the outer wall 3, the sterilization gas conveyance channel 7, and the opening/closing means 12, in this case the two facing side parts 19a and 19b, which remain integral with one another and enclose the sterilized biopharmaceutical contents C.

With this arrangement, and as above, the sterilized biopharmaceutical packaging 1 and the sterilized biopharmaceutical content C can undergo one or more integrity tests at any time desired after sterilization.

Figure 5A:
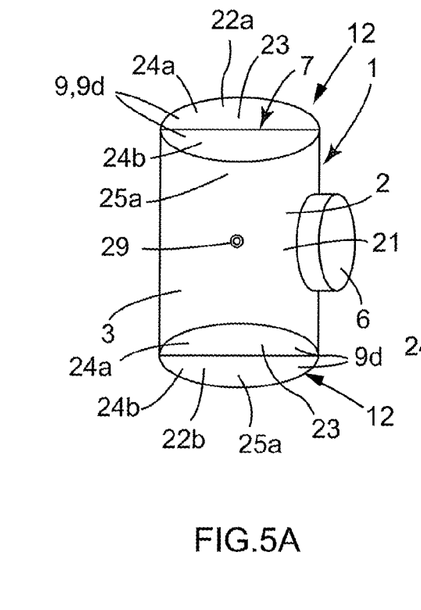
Figure 5B:
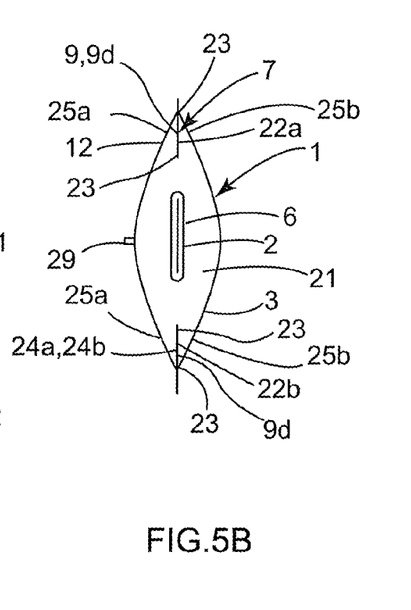

Reference is now made more especially to FIGS. 5A and 5B that illustrate a second variant of the second embodiment with a membrane integrated in the outer wall 3.

In this second variant, the outer wall 3 comprises a side part 21 of cylindrical shape, where the introduction opening 6 and two transverse end surfaces 22a and 22b, circular here, are provided in the deployed state, as is shown in FIG. 5B.

Each of the two transverse end surfaces 22a and 22b can be folded along a diametric folding line 23 toward the inside of the packaging 1, into the folded state, as is shown in FIG. 5B, in such a way that the two transverse end half-surfaces 24a and 24b of each transverse end surface 22a or 22b resulting therefrom are then located opposite the parts 25a and 25b of the cylindrical side part 21.

The deployable/foldable part 18, i.e., here, the two transverse end surfaces 22a and 22b that form the membrane 9d, is capable of either being deployed in such a way that the sterilization gas conveyance channel 7 is open or folded on itself toward the inside of the packaging 1 as a result of two transverse end half-surfaces 24a and 24b with the diametric folding line 23, in such a way that the sterilization gas conveyance channel 7 is then closed.

When the two transverse end half-surfaces 24a and 24b of each of the transverse end surfaces 22a and 22b are folded on one another toward the inside of the packaging 1, they are covered by the two parts 25a and 25b that are diametrically opposite and adjacent to the side part 21, which are located opposite and close together.

The two diametrically opposite parts 25a and 25b are then able to be sealed to one another at their outer periphery, in an airtight manner, around the zone 9d that is permeable to the sterilization gas in the form of membrane 9d. With such a structure, in this case, the two parts 25a and 25b prevent the sterilization gas from accessing the zone 9d that is permeable to the sterilization gas in the form of membrane 9d.

The process for implementing such a packaging 1 is analogous to the one described above with resulting adaptations, aside from the structure of the packaging 1. Thus, once the sterilization is done, the deployable/foldable part 18 is folded; i.e., the two transverse end half-surfaces 24a and 24b of each of the transverse end surfaces 22a and 22b, and the two parts 25a and 25b are sealed around each membrane 9d. The sterilized biopharmaceutical packaging 1 that encloses the sterilized biopharmaceutical contents C is then formed.

As above, the sterilized biopharmaceutical packaging 1 consists of the outer wall 3, the sterilization gas conveyance channel 7, and the opening/closing means 12, in this case the two diametric parts 25a and 25b, which remain integral with one another and enclose the sterilized biopharmaceutical contents C. Such a sterilized biopharmaceutical packaging 1 and the sterilized biopharmaceutical contents C can undergo one or more integrity tests at any time desired after sterilization.

Figure 6:
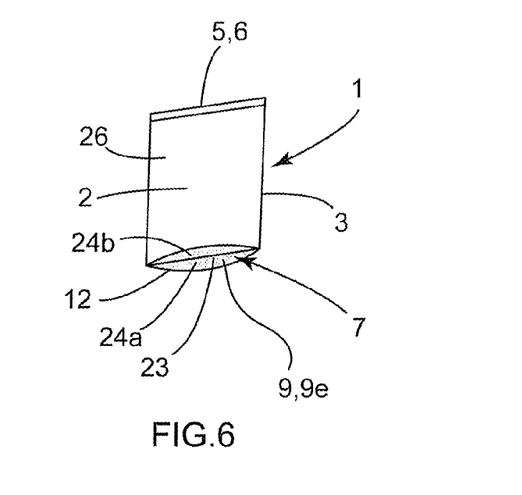
FIG. 6 is a view that is analogous to FIG. 5A in the case of a third example, with the deployable/foldable part of the outer wall of the packaging being deployed here, whereas the means for control of the distribution of sterilization gas in the inside space open the sterilization gas conveyance channel, with the deployable/foldable part of the outer wall of the packaging being formed by a single transverse end part.

Reference is now made more especially to FIG. 6, which illustrates a third variant of the second embodiment with a membrane integrated with the outer wall 3.

This third variant differs from the second in that the outer wall 3 comprises a side part 26 with a cylindrical shape at one end and with a flattened shape at the other end, when the introduction opening 6 is closed.

The part with a cylindrical shape at one end is analogous to one of the transverse end surfaces 22a or 22b, with, consequently, two transverse end half-surfaces 24a and 24b and a diametric folding line 23, forming the membrane 9e that is permeable to sterilization gas.

The part with a flattened shape is open, originally, and constitutes the introduction opening 6 that can be sealed on itself.

With such a structure, it is possible to position the introduction opening 6 at one end of the packaging rather than on the side part 26, as in the second variant.

Reference is now made to FIG. 7, which illustrates a sterilizable biopharmaceutical packaging 1 according to a second embodiment.

In this second embodiment, the outer wall 3 has a general sheath form, as in the embodiment of FIG. 1.

The sterilization gas conveyance channel 7 does not include a membrane that is permeable to sterilization gas, such as the membranes 9a, 9b, 9c, 9d or 9e described above, but one (or, if necessary, several) segment(s) of a sterilization gas intake tube 27.

Such a tube segment 27 is located on the outside of the packaging 1. Upstream, it forms the upstream opening 8 for intake of sterilization gas, and downstream, it forms the downstream opening 9 for distribution of sterilization gas. This opening 9 is provided in the outer wall 3. The segment of the sterilization gas intake tube 27 is integral with the outer wall 3 in an airtight manner.

One (or, if necessary, several) means 28 that is/are capable of stopping any pathogenic germs, such as a filtering cartridge, is inserted in the segment of tube 27 between the upstream intake opening 8 and the downstream distribution opening 9.

With this second embodiment, the means 12 for control of the distribution of sterilization gas are, here also, opening/closing means 12 of the conveyance channel 7, namely a means 12c for stopping the flow, mounted to move on or to be detached from the tube segment 27.

Such a stopping means 12c is, for example, a closing clamp or a transverse weld.

The process for implementing such a packaging 1 is derived from the above-described process in relation to the other embodiments.

A biopharmaceutical packaging 1 with a segment of tube 27, opening/closing means 12 of the sterilization gas conveyance channel 7, here a means for stopping the flow 12c, and biopharmaceutical contents to be sterilized C is used.

After the biopharmaceutical contents have been sterilized, the means for stopping the flow 12c is inserted into the segment of tube 27 in such a way as to close the sterilization gas conveyance channel 7.

As above, the sterilized biopharmaceutical packaging 1 consists of its constituent parts that are integral with one another, without the necessity of having to be cut into sections, in such a way that the sterilized biopharmaceutical packaging 1 and the sterilized biopharmaceutical contents C can undergo one or more integrity tests at any time desired after sterilization.

As above, consequently, the process is such that the constituent parts of the sterilized packaging are kept integral without having to cut it into several parts.

In all of the embodiments shown, the inside space 2 extends over substantially the entire length of the outer wall 3. In addition, except for the embodiment of FIGS. 5A and 5B, the introduction opening 7 is located at one end of the outer wall 3. Other embodiments can, however, be taken into consideration. In contrast, the upstream gas intake opening 8 and the introduction opening 6 of the biopharmaceutical contents to be sterilized C that are to be sterilized are not only separate but separated from one another.

In the embodiments of FIGS. 1, 2, 3, 5A, 5B, it is also provided that the packaging 1 comprises one (or more) gas inlet/outlet end fitting(s) 29.

Such an end fitting 29 is mounted on the outer wall 3. It is in communication with the inside space 2. It is capable of being brought into the open state or into the closed state by actuating suitable closing means, such as stoppering means. It is capable of being associated in communication with a gas source or a gas outlet. Thus, this end fitting 29 makes it possible to enable a functional gas to enter into or exit from the inside space 2, or to create a pressure or an underpressure in the inside space 2.

Such a gas can be, for example, the one that is used for an integrity monitoring process, so as to have a pressure differential between the inside space 2 and the outside environment of the packaging 1.

According to a characteristic of the invention, the process for implementing the packaging 1 is such that once the sterilization is done, the biopharmaceutical packaging 1 is not cut into several segments, which makes it possible to avoid the drawbacks of such a cutting into sections: time taken, technical means for cutting into sections, risk of deterioration of the outer wall 3.

The object of the invention is not only the empty packaging 1 before sterilization of the interior and its contents C, but also the sterilized packaging 1 that encloses sterilized biopharmaceutical contents C, as it was achieved by the implementation of different variants of the process described above.

Such a sterilized packaging 1 that is filled with its sterilized biopharmaceutical contents C also comprises an opening for extracting the sterilized biopharmaceutical contents C from the inside to the outside of the packaging.

This extraction opening is closed in an airtight manner during sterilization. It is subsequently capable of being opened in such a way as to extract the biopharmaceutical contents from the inside space.

Such an extraction opening can be simply a tear or a cut in the outer wall 3.

As indicated, the sterilized biopharmaceutical packaging 1 and the sterilized biopharmaceutical contents C can undergo one or more integrity tests at any time desired after sterilization.

The purpose of the invention is also the process that comprises all of the above-described steps for implementing the sterilized biopharmaceutical packaging 1 with its sterilized biopharmaceutical contents Cs and in which, at any time desired after sterilization, this sterilized biopharmaceutical packaging that encloses the sterilized biopharmaceutical contents C is enabled to undergo one or more integrity tests of the type requiring sealing of the packaging against gas.

According to another characteristic of the invention, one or the other of the embodiments of the biopharmaceutical packaging 1 as described above can also integrate an opening that is delimited by an annular flange on which is mounted a movable or detachable means of aseptic transfer, corresponding to, for example, doors that are used in the double-door type of aseptic transfer devices.

By way of example and in no way limiting, it is possible to cite the devices that are known under the trademark BIOSAFE® and the devices for sealed junction between a first chamber and a second chamber that are insulated from an external environment described in the document EP-A-0688020 that is incorporated by reference.

In addition, it would also be possible to use sealed junction devices that are similar to those known under the trademark BIOSAFE® but that make it possible to implement a large number of successive openings of the movable or detachable means of aseptic transfer.

According to different variant embodiments, this movable or detachable means of aseptic transfer can either work with the introduction opening 6 to ensure the closing of this introduction opening 6 in an airtight manner or work with a portion of the outer wall 3 that is separate from the membrane 9 that is permeable to the sterilization gas in such a way as to form a secondary opening that is capable of being opened and then closed in an airtight manner.

It thus is possible to transfer the sterilized biopharmaceutical contents enclosed inside the biopharmaceutical packaging 1 through the movable or detachable aseptic transfer means and toward an insulated chamber without running the risk that said sterilized biopharmaceutical contents will be brought into contact with the outside environment and contaminated by it.

Such an embodiment thus makes it possible also to reduce the risks of contamination of the biopharmaceutical contents after the latter have been sterilized.

The invention claimed is:

1. A sterilizable biopharmaceutical packaging, capable of enclosing biopharmaceutical contents to be sterilized, comprising:
    an outer wall that is flexible and sealed against gases and pathogenic germs,
    an opening for introduction of the biopharmaceutical contents to be sterilized from the outside to the inside of the packaging, as a result capable of being closed in an airtight manner,
    an inside space that is capable of receiving the biopharmaceutical contents, a sterilization gas conveyance channel from the outside of the packaging, comprising at least one upstream intake opening that is capable of being associated in communication with a sterilization gas source, at least one downstream opening for distribution of sterilization gas emptying into the inside space, and a communication between the upstream intake opening and the downstream distribution opening,
    with the introduction opening being separate from the conveyance channel and directly adjacent to the inside space,
    and means for control of the distribution of sterilization gas in the inside space being means for opening/closing the conveyance channel wherein:
    the conveyance channel includes at least one large-surface membrane that is permeable to the sterilization gas, forming a downstream opening for distribution of sterilization gas distributed over the surface of the membrane, the membrane forming a part of the envelope of the inside space and constituting a filtering means that is capable of stopping any pathogenic germs,
    with the means for opening/closing the conveyance channel being either a stoppering element or the outer wall folded on itself and sealed in an airtight manner,
    once the sterilization is done, the outer wall, the sterilization gas conveyance channel, and the opening/closing means remain integral with one another in such a way as to form a sterilized biopharmaceutical packaging that encloses the sterilized biopharmaceutical contents that can undergo one or more integrity tests of the type with differential pressure requiring sealing of the packaging against gas at any time desired after sterilization.

2. The sterilizable biopharmaceutical packaging according to claim 1, wherein a membrane that is permeable to sterilization gas is separate from the outer wall of the packaging and connected to it, in it, and made integral with it in an airtight manner, with the outer wall comprising an upstream opening for intake of sterilization gas that is bounded by a ring, with communication existing between the upstream intake opening and the membrane.

3. The sterilizable biopharmaceutical packaging according to claim 2, wherein the membrane that is permeable to sterilization gas extends substantially opposite the upstream intake opening.

4. The sterilizable biopharmaceutical packaging according to claim 1, in which the membrane that is permeable to sterilization gas extends over at least substantially the entire length of the outer wall of the packaging.

5. The sterilizable biopharmaceutical packaging according to claim 2, wherein the opening/closing means are a stoppering element that is mounted to move on or to be detached from the ring of the upstream opening for intake of sterilization gas.

6. The sterilizable biopharmaceutical packaging according to claim 1, wherein a membrane that is permeable to sterilization gas consists of a permeable zone of the outer wall of the packaging that belongs to a deployable/foldable part of the outer wall of the packaging and that forms the sterilization gas conveyance channel, with this deployable/foldable part being capable of being either deployed in such a way that the sterilization gas conveyance channel is open, or folded on itself toward the inside of the packaging in such a way that the sterilization gas conveyance channel is closed.

7. The sterilizable biopharmaceutical packaging according to claim 6, wherein the part of the outer wall of the packaging that is capable of being either in the deployed state or in the state folded on itself toward the inside is a longitudinal gusset of the outer wall.

8. The sterilizable biopharmaceutical packaging according to claim 6, wherein the part of the outer wall of the packaging that is capable of either being in the deployed state or in the state folded on itself toward the inside is a transverse end part of the outer wall.

9. The sterilizable biopharmaceutical packaging according to claim 6, wherein the opening/closing means consist of the outer wall itself, whose deployable/foldable part where the zone that is permeable to sterilization gas is located is inserted between two airtight facing side parts located on both sides of the deployable/foldable part, in such a way that when the deployable/foldable part is folded on itself toward the inside of the packaging, the two facing side parts, then located opposite and close together, are capable of being sealed to one another on their outer periphery in an airtight manner, around the zone that is permeable to the sterilization gas, in such a way as to prevent the sterilization gas from accessing the permeable zone.

10. The sterilizable biopharmaceutical packaging according to claim 1, wherein the inside space extends over substantially the entire length of the outer wall in sheath form, and in which the introduction opening of the biopharmaceutical contents to be sterilized is located at one end of the outer wall in sheath form.

11. The sterilizable biopharmaceutical packaging according to claim 1, wherein the at least one upstream opening for intake of gas and the introduction opening of the biopharmaceutical contents to be sterilized are separated from one another.

12. The sterilizable biopharmaceutical packaging according to claim 1, which also comprises at least one gas inlet/outlet end fitting, mounted on the outer wall, in communication with the inside space, able to be brought into the open state or into the closed state by actuating closing means in such a way as to make it possible to enable a functional gas to enter into or exit from the inside space.

13. The sterilizable biopharmaceutical packaging according to claim 1, also comprising an opening that is delimited by an annular flange on which is mounted a movable or detachable means of aseptic transfer, such as a movable or detachable door for aseptic transfer of the double-door type.

14. The sterilizable biopharmaceutical packaging according to claim 13, wherein the movable or detachable means for aseptic transfer works with the introduction opening and is capable of ensuring the closing of this introduction opening in an airtight manner.

15. The sterilizable biopharmaceutical packaging according to claim 13, wherein the movable or detachable means for aseptic transfer works with a portion of the outer wall that is separate from the membrane that is permeable to sterilization gas in such a way as to form a secondary opening that is capable of being opened and then closed in an airtight manner.

16. A process for implementing a sterilizable biopharmaceutical packaging according to claim 1, for the purpose of enclosing and sterilizing biopharmaceutical contents therein, wherein:
such a packaging, empty of biopharmaceutical contents, and whose introduction opening is open, is used,
the biopharmaceutical contents to be sterilized are used,
a sterilization gas source is used,
via the introduction opening, the biopharmaceutical contents to be sterilized are introduced directly into the inside receiving space,
then, the introduction opening is closed in an airtight manner,
then, whereas the sterilization gas conveyance channel is open, the sterilization gas is brought in from the sterilization gas source to the inside receiving space where the biopharmaceutical contents to be sterilized are located, in such a way as to sterilize the biopharmaceutical contents,
then, the opening/closing means are implemented, being either a stoppering element or the outer wall folded on itself and sealed in an airtight manner in such a way as to close the sterilization gas conveyance channel, the sterilization gas conveyance channel and the opening/closing means remaining integral with one another,
and thus a sterilized biopharmaceutical packaging is formed that encloses the sterilized biopharmaceutical contents that can undergo one or more integrity tests of the type with differential pressure requiring sealing of the packaging against gas at any time desired after sterilization.

17. The process according to claim 16, wherein:
a membrane that is permeable to sterilization gas and that is separate from the outer wall, is used, and opening/closing means that are a stoppering element are used,
and, after the biopharmaceutical contents have been sterilized, the stoppering element is implemented on a ring of the upstream opening for intake of sterilization gas in such a way as to close the sterilization gas conveyance channel.

18. The process according to claim 16, wherein:
a membrane that is permeable to sterilization gas constituted by a permeable zone of the outer wall of the packaging belonging to a deployable/foldable part, and opening/closing means that consist of the outer wall whose deployable/foldable part is inserted between two airtight facing side parts are used,
and, after the biopharmaceutical contents have been sterilized, the deployable/foldable part is folded on itself toward the inside of the packaging, in such a way that the two facing side parts are located opposite and close together, and they are sealed to one another on their outer periphery in an airtight manner, around the zone that is permeable to the sterilization gas, in such a way as to close the sterilization gas conveyance channel.

19. The process according to claim 16, wherein once the sterilization is done, the outer wall, the sterilization gas conveyance channel, and the opening/closing means are kept integral in such a way as to form the sterilized biopharmaceutical packaging that encloses the sterilized biopharmaceutical contents.

20. The process according to claim 19, wherein once the sterilization is done, the biopharmaceutical packaging is not cut into several segments.

21. The process according to claim 16, wherein at any time desired after sterilization, the sterilized biopharmaceutical packaging that encloses the sterilized biopharmaceutical contents is made to undergo one or more integrity tests of the type requiring sealing of the packaging against gas.

22. A sterilized biopharmaceutical packaging that encloses sterilized biopharmaceutical contents, wherein it is obtained by implementing the process according to claim 16, with the packaging also comprising an opening for extracting, from the inside to the outside of the packaging, the sterilized biopharmaceutical contents, closed in an airtight manner and subsequently capable of being opened in such a way as to extract the biopharmaceutical contents from the inside space.

* * * * *